United States Patent [19]

Heilen et al.

[11] 4,273,945

[45] Jun. 16, 1981

[54] PREPARATION OF SATURATED ALIPHATIC, CYCLOALIPHATIC AND ARALIPHATIC ALDEHYDES

[75] Inventors: Gerd Heilen, Speyer; Axel Nissen, Leimen; Wolfgang Köernig, Dossenheim; Michael Horner, Neustadt; Werner Fliege, Otterstadt; Güenter Boettger, Bad Durkheim, all of Fed. Rep. of Germany

[73] Assignee: BASF Aktiengesellschaft, Fed. Rep. of Germany

[21] Appl. No.: 54,889

[22] Filed: Jul. 5, 1979

[30] Foreign Application Priority Data

Jul. 26, 1978 [DE] Fed. Rep. of Germany ....... 2832699

[51] Int. Cl.$^3$ .............................................. C07C 45/62
[52] U.S. Cl. .................................... 568/420; 568/434; 568/462; 252/462
[58] Field of Search .................... 260/601 R; 568/462, 568/434, 420

[56] References Cited

U.S. PATENT DOCUMENTS

| 3,118,954 | 1/1964 | Robbins et al. | 260/601 R X |
| 4,146,581 | 3/1979 | Nissen et al. | 210/601 R X |

FOREIGN PATENT DOCUMENTS

| 1025047 | 4/1966 | United Kingdom | 260/601 R |
| 1065395 | 4/1967 | United Kingdom . | |
| 1065628 | 4/1967 | United Kingdom | 260/601 R |
| 1310143 | 3/1973 | United Kingdom . | |

OTHER PUBLICATIONS

Rylander et al., Engelhard Ind. Tech. Bull., vol. 4, (1963) pp. 49-51.

Primary Examiner—Bernard Helfin
Attorney, Agent, or Firm—Keil & Witherspoon

[57] ABSTRACT

Saturated aliphatic, cycloaliphatic and araliphatic aldehydes are prepared by selective hydrogenation of the corresponding olefinically unsaturated aldehydes with hydrogen in the liquid phase over a palladium-containing catalyst, using a catalyst system in which the active constituents are from 2 to 90% by weight of palladium and from 10 to 98% by weight of an oxide or a salt of a rare earth metal or of a mixture of different oxides and/or salts of this type.

3 Claims, No Drawings

PREPARATION OF SATURATED ALIPHATIC, CYCLOALIPHATIC AND ARALIPHATIC ALDEHYDES

The present invention relates to a novel process for the preparation of saturated aliphatic, cycloaliphatic and araliphatic aldehydes by selective hydrogenation of the corresponding olefinically unsaturated aldehydes with hydrogen in the liquid phase over a palladium-containing catalyst.

The selective hydrogenation of olefinically unsaturated aldehydes, under conditions which preserve the aldehyde group, forms the subject of numerous investigations and process descriptions. For example, French Pat. No. 1,399,393 discloses the quantitative conversion of crotonaldehyde to butyraldehyde in the liquid phase, under atmospheric or slightly superatmospheric pressure, at from 25° to 65° C., over palladium/charcoal or palladium/alumina. Though these mild reaction conditions are desirable, they have the disadvantage, for industrial synthesis, of requiring a relatively long reaction time. Under more severe reaction conditions, the said catalysts on the other hand prove too active and in part also cause hydrogenation of the aldehyde group.

Further, German Pat. No. 1,941,634 discloses the hydrogenation of 2-ethylhex-2-en-1-al to 2-ethylhexan-1-al at 200 bar and 90° C., using a special palladium/silica catalyst. However, this catalyst has a relatively low activity and therefore gives somewhat unsatisfactory reaction times, in spite of the high pressure required.

It is furthermore a factor common to these and numerous other processes for the partial hydrogenation of olefinically unsaturated aldehydes, using various catalysts under various reaction conditions, that they are only satisfactory in specific cases and are not universally applicable. This is technically and economically a considerable disadvantage, since it requires the preparation and stockage of a variety of catalysts, and in most cases also requires the setting up of several different hydrogenation installations. This may not be a disadvantage where heavy chemical products, produced with full plant capacity utilization throughout the year, are involved, but it is a disadvantage where—as is frequently the case in practice—several special products, only required in relatively small amounts, are involved. In such cases it would be desirable to carry out the various hydrogenations in one and the same plant, using substantially identical reaction conditions and using one and the same catalyst.

It is an object of the present invention to meet this requirement and to improve the art of the reaction in question by providing a universally applicable, highly active and nevertheless selective catalyst. Specifically, this object applies to the selective hydrogenation of α,β-unsaturated aldehydes, which are particularly prone to perhydrogenation, to give the corresponding saturated aldehydes.

We have found that this object is achieved by a process for the preparation of saturated aliphatic, cycloaliphatic and araliphatic aldehydes by selective hydrogenation of the corresponding olefinically unsaturated aldehydes with hydrogen in the liquid phase over a palladium-containing catalyst, wherein a catalyst system is used, of which the active constituents consist of 2-90% by weight of palladium and 10-98% by weight of an oxide or salt of a rare earth metal or of a mixture of different oxides and/or salts of this type.

Catalyst systems of this type are described in German Laid-Open Application DOS No. 2,615,308, where they are proposed for the condensation of aldehydes with ketones and simultaneous hydrogenation of the unsaturated ketones transiently produced thereby. It was not to be expected that these catalyst systems would also be successfully applicable to the selective hydrogenation of olefinically unsaturated aldehydes, since the aldehyde group is more sensitive than the keto group and hence perhydrogenation of the olefinically unsaturated aldehydes to the corresponding saturated alcohols might have been expected.

Suitable active components used additionally to palladium are all oxides and salts of the rare earth metals (hereafter referred to as RE compounds), and amongst these preferably the oxides, more especially lanthanum oxide ($La_2O_3$), samarium oxide ($Sm_2O_3$), gadolinium oxide ($Gd_2O_3$) and holmium oxide ($Ho_2O_3$) and very particularly cerium oxide ($CeO_2$), praseodymium oxide ($Pr_2O_3$) and neodymium oxide ($Nd_2O_3$).

Instead of the oxides it is also possible to use, according to the invention, salts of the rare earth metals, for example the nitrates, sulfates, phosphates, chlorides and carbonates. However, the salts of organic acids, such as the acetates, propionates, phenolates, benzenesulfonates and toluenesulfonates and especially the organic salts of the higher fatty acids, for example of stearic acid, are preferred. If the salts are soluble in the starting compound to be hydrogenated, they can be added before the reaction, and then the resulting mixture merely has to be passed over a conventional palladium catalyst. This process is particularly advisable in cases where a hydrogenation carried out over an already existing conventional palladium catalyst is to be switched over to the hydrogenation according to the invention without the expense of changing the catalyst. After the hydrogenation, the product merely has to be distilled from the RE salt.

Furthermore, it is not necessary to use the pure RE compounds. Instead, their mixtures, for example the commercial RE oxides and RE salts of technical-grade purity, containing about 90% by weight of an RE oxide or salt, the remainder consisting of a plurality of other RE compounds, are equally suitable.

The use of the term catalyst system is intended to make clear that it is merely important that the two components palladium and RE compound should be present simultaneously during the hydrogenation. Accordingly, the effect desired according to the invention manifests itself even if the palladium and the RE compound are present conjointly in a suspension of the aldehyde to be hydrogenated, or in an organic solution of this aldehyde. The same remarks apply where a suspension of a supported Pd catalyst, for example with active charcoal as the carrier, and a supported RE oxide catalyst, for example with alumina as the carrier, is concerned.

Such methods are feasible in principle and are frequently also suitable for hydrogenations on a laboratory scale or pilot-plant scale. For continuous industrial operation it is however advisable, for well-known technological reasons, to arrange the catalyst as a fixed bed in a reactor column and to pass hydrogen and the aldehyde, or a solution of the aldehyde, over such a bed.

For this purpose, it is preferred to use a supported catalyst which carries both the palladium and the RE compound. Such supported catalysts can be prepared by impregnating the carrier with an aqueous solution which contains a Pd salt, eg. palladium nitrate, and an RE salt, in the appropriate ratio, and then drying the product and heating it in a stream of air, whereupon the RE oxide is formed. The Pd metal subsequently forms automatically under the hydrogenating conditions, but can also be formed by subjecting the supported catalyst to a separate hydrogenation.

Examples of suitable carriers are active charcoal, alumina and silica gel in the form of tablets, granules, beads and extrudates having diameters of 2–20 mm and lengths of 5–50 mm.

A loose bed of 1 liter of such a supported catalyst contains about 4–80 g of active catalyst constituents, depending on the geometrical shape and total surface area of the carrier.

In general, the weight ratio of Pd to RE compound is 2:98–90:10, but as a rule catalysts in which this ratio is from 20:80 to 80:20 are preferred.

The quantitative or virtually quantitative selective hydrogenation of 1 mole of the olefinically unsaturated aldehyde at 100° C. under a hydrogen pressure of 10 bar requires, depending on the catalyst shape, from about 2 to 10 ml of one of the above supported catalysts, the reaction time being about 2–10 hours. These are guideline values which vary with the reaction conditions in accordance with the well-known laws, as can easily be established by a few experiments. The reaction conditions are substantially independent of the nature of the aldehyde to be hydrogenated, so that the process according to the invention allows the hydrogenation of different olefinically unsaturated aldehydes in one and the same installation, without changing the catalyst.

The process proves successful even at atmospheric pressure but pressures of up to 100 bar can also be used in order to increase the rate of reaction. Even higher pressures normally offer no further advantages proportionate to the technical effort involved. In general, the economically most advantageous results are achieved with pressures of from 1 to 50 bar.

Suitable reaction temperatures are from 20° to 250° C., preferably from 20° to 220° C. At lower temperatures than 20° C., the rate of hydrogenation drops substantially, whilst above 250° C. side-reactions, especially aldol condensations, increasingly impose limitations. Remarkably, only a slight increase in the hydrogenation of the aldehydes to the alcohols is encountered even at higher temperatures, as long as the hydrogenation of the olefinic double bond is not yet complete. Accordingly, the selectivity of the catalysts according to the invention is substantially temperature-independent and this is to be regarded as a special advantage.

If the olefinically unsaturated aldehydes to be hydrogenated are liquid under the reaction conditions, it is unnecessary to use a solvent, though the presence of a solvent can be an advantage even in such cases, inasmuch as it counteracts side-reactions, such as aldol condensations. If the aldehydes are solid, they must be used in the form of solutions.

Suitable solvents are all liquids which are inert under the reaction conditions, for example $C_5$–$C_8$-paraffins, cyclohexane, methanol, ethanol, isopropanol, ethyl acetate, toluene and xylene.

The amount of solvent is not critical and is usually from 0.5 to 10 times the amount of aldehyde.

The process is applicable to all olefinically unsaturated aldehydes and is therefore fundamentally not subject to any limitations. If these aldehydes possess substituents which could also undergo hydrogenation—for example acyl groups—there is no danger of such hydrogenation taking place, particularly since the aldehyde group is also not attacked. If the aldehydes contain several olefinic double bonds, all these become saturated.

If the aldehyde group is conjugated with the double bond, the aldehyde group is normally particularly easily attacked and hydrogenated to the alcohol group. This effect, which is undesirable if the objective is selective hydrogenation, hardly occurs in the process according to the invention, so that the process is of very great importance for such cases, namely for hydrogenating $\alpha,\beta$-unsaturated aldehydes to the corresponding saturated aldehydes.

Industrially important saturated aldehydes are especially those where the hydrocarbon radical is of 4 to 20 carbon atoms. The following are examples of olefinically unsaturated aldehydes which serve as starting materials for the preparation of the said saturated aldehydes:

aliphatic $\alpha,\beta$-olefinically unsaturated aldehydes, eg. crotonaldehyde, 2-methylpent-2-en-1-al, 2-methylbut-2-en-1-al, 3-methylbut-2-en-1-al, 2-ethylhex-2-en-1-al, citral (3,7-dimethylocta-2,6-dien-1-al) and citronellal (3,7-dimethyloct-6-en-1-al);

aliphatic olefinically unsaturated aldehydes with an isolated double bond, eg. 3-methylbut-3-en-1-ol;

cycloaliphatic olefinically unsaturated aldehydes, eg. 1-formylcyclohex-3-ene; and araliphatic olefinically unsaturated aldehydes, eg. cinnamaldehyde, $\alpha$-methylcinnamaldehyde, p-isopropyl-$\alpha$-methylcinnamaldehyde and p-tert.-butyl-$\alpha$-methylcinnamaldehyde.

Some of the products obtainable by the novel process are important intermediates for industrial chemicals, for example butyraldehyde, obtained from crotonaldehyde, for the preparation of the plasticizer alcohol 2-ethylhexanol, and 2-ethylhexanal, from 2-ethylhexenal, for the preparation of 2-ethylhexanoic acid, whilst some, for example 3,7-dimethyloctanal from crital, are intermediates for scents of the aldehyde series.

EXAMPLE 1

Preparation of various supported catalysts 2,400 g portions of 4 mm thick extrudates of a carrier were impregnated with 2,500 ml of an aqueous nitric acid solution containing the amounts of palladium nitrate and an RE nitrate which corresponded to the composition of the finished catalyst. On impregnation, the solution was completely absorbed by the carrier. After impregnation, the extrudates were dried for 16 hours at 120° C. and then heated for 6 hours at 520° C., whereby the RE nitrates were converted to the RE oxides. The extrudates were then broken into 2 cm lengths.

The characteristics of the catalysts are shown in Table 1.

TABLE 1

Characteristics of the various supported catalysts according to Example 1

| Catalyst | Carrier | RE oxide | Content in % by weight, based on the total amount of catalyst, of Pd | RE oxide | Ratio Pd:RE oxide |
|---|---|---|---|---|---|
| according to the invention | | | | | |
| A | $\gamma$—$Al_2O_3$ | $Pr_2O_3$ | 0.5 | 5.0 | 9:91 |
| B | $\gamma$—$Al_2O_3$ | $Pr_2O_3$ | 5.0 | 5.0 | 50:50 |
| C | $\gamma$—$Al_2O_3$ | $CeO_2$ | 0.1 | 5.0 | 2:98 |
| D | $SiO_2$ | $Pr_2O_3$ | 0.07 | 0.5 | 12:88 |
| for comparison | | | | | |
| E | $SiO_2$ | — | 0.07 | — | — |
| F | $\gamma$—$Al_2O_3$ | — | 0.3 | — | — |
| G | $\gamma$—$Al_2O_3$ | — | 5.0 | — | — |

EXAMPLE 2

Hydrogenation of 2-ethylhex-2-en-1-al

Several experiments were carried out on the hydrogenation of 50 g per hour of 2-ethylhex-2-en-1-al in a trickle reactor of 0.5 l capacity, under the reaction conditions shown in Table 2. The conversions and yields, also shown in the Table, were determined by gas chromatography.

EXAMPLE 3

Hydrogenation of citral

In each case, 152 g of citral (3,7-dimethylocta-2,6-dien-1-al) were hydrogenated with 3 g of a catalyst, in a stirred autoclave of 300 ml capacity, until no further hydrogen was absorbed, ie. until 100% conversion had been reached. Details of the experimental conditions and of the outcome of the process are shown in Table 3. The yields were determined by gas chromatography.

EXAMPLES 4 TO 9

Hydrogenation of various unsaturated aldehydes

Using a method similar to Example 3, 150 g of an unsaturated aldehyde were in each case hydrogenated with 3 g of catalyst A until conversion was virtually complete. The process conditions and results are shown in Table 4. The yields were determined by gas chromatography.

EXAMPLE 10

150 g of a 10% strength by weight solution of 4-tert.-butyl-$\alpha$-methylcinnamaldehyde in methanol were selectively hydrogenated under a hydrogen pressure of 15 bar, at 110° C., in the presence of a mixture of 1 g of a Pd/active charcoal catalyst, containing 10% by weight of Pd, and 1 g of neodymium stearate. After 6 hours, conversion was virtually complete. The yield of 3-(4-tert.-butylphenyl)-2-methylpropanal, determined by gas chromatography, was 98%.

TABLE 2

Reaction conditions and results of the experiments of Example 2 on the hydrogenation of 2-ethylhex-2-en-1-al

| Experiment No. | Catalyst | Hydrogen pressure (bar) | Temperature (°C.) | Conversion (%) | Yield of 2-ethylhexanal based on conversion (%) | Yield of 2-ethylhexanal based on absolute (%) | Yield of 2-ethylhexanol absolute (%) |
|---|---|---|---|---|---|---|---|
| according to the invention | | | | | | | |
| 1 | A | 10 | 80 | 96 | 99 | 94 | in all cases <1 |
| 2 | A | 10 | 100 | 96 | 98 | 95 | |
| 3 | A | 10 | 115 | 98 | 98 | 97 | |
| 4 | A | 15 | 80 | 99 | 99 | 98 | |
| 5 | A | 15 | 100 | 99 | 98 | 97 | |
| 6 | A | 15 | 115 | 100 | 98 | 98 | |
| 7 | A | 35 | 80 | 99 | 99 | 98 | |
| 8 | A | 35 | 100 | 98 | 98 | | |
| 9 | A | 35 | 115 | 100 | 98 | 98 | |
| 10 | C | 15 | 80 | 96 | 99 | 95 | |
| 11 | C | 15 | 100 | 97 | 99 | 96 | |
| 12 | C | 15 | 115 | 99 | 98 | 97 | |
| 13 | C | 15 | 150 | 100 | 97 | 97 | |
| 14 | D | 15 | 80 | 95 | 99 | 94 | |
| 15 | D | 15 | 100 | 97 | 99 | 96 | |
| 16 | D | 15 | 115 | 98 | 99 | 97 | |
| conventional | | | | | | | |
| 17 | E | 15 | 100 | 40 | 92 | 37 | |
| 18 | E | 35 | 100 | 52 | 92 | 48 | |
| 19 | F | 35 | 115 | 50 | 98 | 45 | |

TABLE 3

Reaction conditions and results of the experiments of Example 3 on the hydrogenation of citral

| Experiment No. | Catalyst | Solvent | Hydrogen pressure (bar) | Temperature (°C.) | Duration (h) | Yield (%) of 3,7-dimethyl-octanal | Yield (%) of 3,7-dimethyl-oct-6-en-1-al | 3,7-dimethyl-octanol |
|---|---|---|---|---|---|---|---|---|
| according to the invention | | | | | | | | |
| 1 | B | none | 40 | 100 | 10 | 96 | 2 | <1 |
| 2 | B | none | 20 | 40 | 16 | 96 | 3 | <1 |
| 3 | B | 60 ml of methanol | 40 | 100 | 7 | 93 | 6 | <1 |
| conventional | | | | | | | | |

TABLE 3-continued

Reaction conditions and results of the experiments of Example 3 on the hydrogenation of citral

| Experiment No. | Catalyst | Solvent | Hydrogen pressure (bar) | Temperature (°C.) | Duration (h) | Yield (%) of 3,7-dimethyl-octanal | Yield (%) of 3,7-dimethyl-oct-6-en-1-al | 3,7-dimethyl-octanol |
|---|---|---|---|---|---|---|---|---|
| 4 | G | 60 ml of methanol | 40 | 100 | 7 | 20 | 66 | 4 |

TABLE 4

Hydrogenation of various unsaturated aldehydes
Examples 4-9

| Example No. | Unsaturated aldehyde | Hydrogen pressure (bar) | Temperature (°C.) | Duration (h) | Yield in (%) of saturated aldehyde | Yield in (%) of saturated alcohol |
|---|---|---|---|---|---|---|
| 4 | 2-methylpent-2-en-1-al 3,7-dimethyloct-6-en-1-al | 160 | 3 | 95 | 1 | |
| 5 | 3,4-dimethyloct-6-en-1-al | 40 | 100 | 8 | 98 | 1 |
| 6 | formylcyclohex-3-ene | 20 | 130 | 6 | 95 | 2 |
| 7 | α-methylcinnamaldehyde | 17 | 120 | 7 | 97 | 1 |
| 8 | 4-tert.-butyl-α-methyl-cinnamaldehyde | 20 | 100 | 8 | 97 | 1 |
| 9 | 4-isopropyl-α-methyl-cinnamaldehyde | 20 | 110 | 7 | 98 | 1 |

We claim:

1. In a process for the preparation of saturated aliphatic, cycloaliphatic and araliphatic aldehydes by selective hydrogenation of the corresponding olefinically unsaturated aldehydes with hydrogen in the liquid phase over a palladium-containing catalyst at a pressure of from 1 to 100 bar and at a temperature of from 20° to 250° C., the improvement which comprises using a catalyst in which the active constituents consist essentially of (a) 2-90% by weight of palladium and (b) 10-98% by weight of an oxide or salt of a rare earth metal or a mixture consisting essentially of oxides and/or salts of rare earth metals, the weight ratio of Pd to rare earth metal being from 2:98 to 90:10.

2. The process of claim 1 wherein the rare earth metal is selected from the group consisting of cerium, praseodymium and neodymium.

3. The process of claim 2 wherein the weight ratio of palladium to rare earth metal is from 20:80 to 80:20.

* * * * *